US007822458B2

(12) United States Patent
Webster, III et al.

(10) Patent No.: US 7,822,458 B2
(45) Date of Patent: Oct. 26, 2010

(54) DISTAL BEVEL-TIP NEEDLE CONTROL DEVICE AND ALGORITHM

(75) Inventors: Robert J. Webster, III, Baltimore, MD (US); Allison M. Okamura, Ruxton, MD (US); Noah J. Cowan, Baltimore, MD (US); Gregory Chirikjian, Towson, MD (US); Kenneth Y. Goldberg, San Francisco, CA (US); Ron Alterovitz, Berkeley, CA (US)

(73) Assignee: The Johns Hopkins University, Baltimore, MD (US)

( * ) Notice: Subject to any disclaimer, the term of this patent is extended or adjusted under 35 U.S.C. 154(b) by 1035 days.

(21) Appl. No.: 11/436,995

(22) Filed: May 19, 2006

(65) Prior Publication Data

US 2007/0016067 A1   Jan. 18, 2007

Related U.S. Application Data

(60) Provisional application No. 60/682,744, filed on May 19, 2005.

(51) Int. Cl.
*A61B 5/05* (2006.01)
(52) U.S. Cl. .................................................... 600/407
(58) Field of Classification Search ................. 600/407, 600/568, 464
See application file for complete search history.

(56) References Cited

U.S. PATENT DOCUMENTS 6,558,309 B2 * 5/2003 Hogendijk et al. ............. 600/7

2005/0203413 A1 * 9/2005 Fichtinger et al. ........... 600/461

OTHER PUBLICATIONS

Okazawa, S., et al., *Hand-Held Steerable Needle Device*, IEEE/ASME Transactions on Mechatronics, vol. 10, No. 3, 2005, pp. 285-296.
Lefrançois, R., et al., Technical Note: *A medical needle drive for the study of interstitial implant mechanics*, Medical Engineering & Physics 25 (2003) pp. 255-258.
Glozman, D., et al., *Flexible Needle Steering and Optimal Trajectory Planning for Percutaneous Therapies*, MICCAI 2004, pp. 137-144.
Ebrahimi, R., et al., *Hand-Held Steerable Needle Device*, MICCAI 2003, pp. 223-230.
DiMaio, S.P., et al., *Needle Steering and Model-Based Trajectory Planning*, MICCAI 2003, pp. 33-40.

* cited by examiner

*Primary Examiner*—Long V Le
*Assistant Examiner*—Saurel J Selkin
(74) *Attorney, Agent, or Firm*—Venable LLP; Henry J. Daley; Steven J. Schwarz

(57) ABSTRACT

Disclosed is a system for percutaneously steering a surgical needle. Needle steering is accomplished by taking advantage of a deflection force imparted on the bevel tip of the needle by the tissue medium as the needle is pushed through the tissue. By controlling the translation speed and rotation angle of the bevel, a flexible needle may be steered substantially without deflecting or distorting the tissue. The control inputs (translation speed and rotation angle) are computed based on a "bicycle" non-holonomic kinematic model that is a function of mechanical properties of the tissue medium. The system may be used with image-based feedback, which may provide for feedback-based refinement of the model as the needle propagates through the tissue.

12 Claims, 7 Drawing Sheets

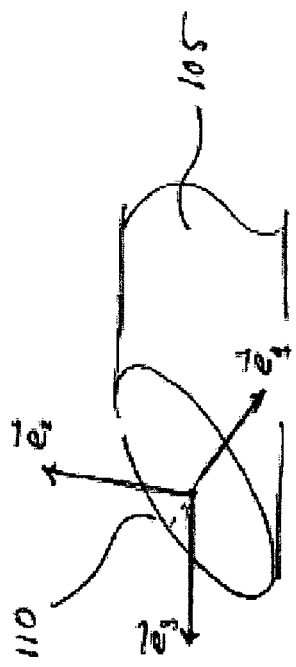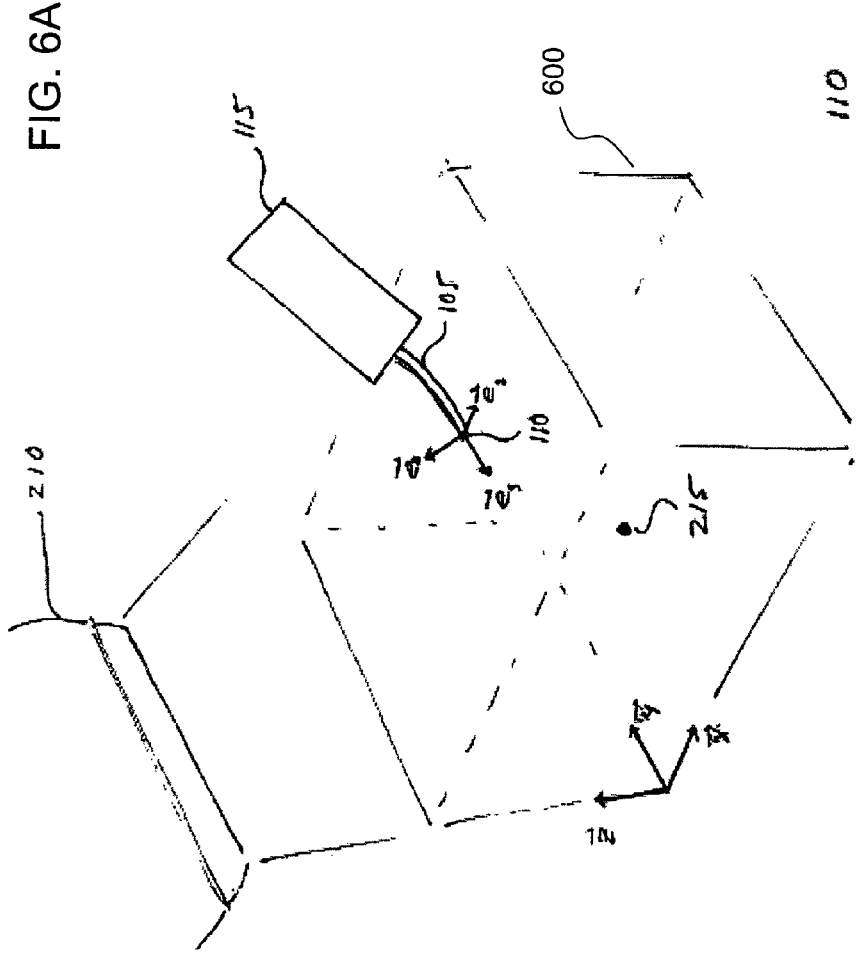

DISTAL BEVEL-TIP NEEDLE CONTROL DEVICE AND ALGORITHM

This application claims the benefit of U.S. Provisional Patent Application No. 60/682,744, filed on May 19, 2005, which is hereby incorporated by reference for all purposes as if fully set forth herein.

The research and development effort associated with the subject matter of this patent application was supported by the National Institutes of Health under Grant No. R21 EB003452 and a National Defense Science and Engineering Graduate Fellowship.

BACKGROUND OF THE INVENTION

1. Field of the Invention

The present invention generally relates to devices and techniques for guiding surgical needles. More particularly, the present invention relates to devices and techniques for percutaneously steering a surgical needle within a tissue medium.

2. Discussion of the Related Art

Accurate and precise needle insertion is an important aspect of many types of medical diagnoses and treatments. Accurate and precise needle placement is required in the treatment of afflictions including, for example, prostate cancer, liver cancer, and intracranial hemorrhage (ICH).

Needle biopsy for prostate cancer is performed on approximately 1.5 million men per year. A common treatment option is transperineal brachytherapy, which involves implanting thin needles to deposit radioactive seeds within the prostate. Precise placement of radioactive seeds is made difficult by organ deflection, dislocation and deformation. Further, significant seed placement error can occur if the needle is tangential to the prostate capsule wall upon penetration. This is generally due to the fact that the prostate's mechanical properties are considerably different from that of the surrounding tissue. According to the related art, needles for delivering radioactive seeds are substantially rigid. As such, accurate and precise needle insertion may be hampered by prostate deflection, dislocation, and deformation. The resulting inaccuracy may hinder optimal application of a radiation dose.

Hepatocellular (liver) cancer is one of the most common cancers in the world, and one of the deadliest. Liver tumors are often treated with thermal ablation administered at the tip of a needle inserted through the skin under the guidance of ultrasound imagery. Liver tumors often have very different mechanical properties than the surrounding tissue, similarly to the aforementioned difficulties in penetrating a prostate capsule. Accordingly, liver tumors are generally difficult to penetrate.

Thermal ablative treatment of liver cancer is further complicated by the typical need for multiple overlapping thermal treatments of a tumor. According to the related art, rigid thermal ablative needles must be removed and reinserted to penetrate the tumor from different angles.

Intracranial hemmorhage (ICH) occurs in roughly 10 to 20 persons out of 100,000. Untreated clot resolution generally takes two to three weeks, with a mortality rate of approximately 50-75%. Related art treatments involve introducing a needle (through a burr hole drilled in the skull) for injecting drugs. The burr hole is generally drilled by freehand. Depending on the surgeon's hand-eye coordination, the burr hole may be misplaced, thereby resulting in the needle path being off as much as 20-25 degrees. To compensate, the burr hole is generally made significantly larger than otherwise necessary, which can lead to technical and clinical complications. The larger burr hole is generally required because the needle is substantially rigid, and is not capable of being steered within the brain.

In all of the above cases, the needles are generally rigid and are typically inserted by hand. Any initial misplacement or misalignment of the needle requires that the needle be pushed through the tissue medium in such a way that the tissue medium is distorted. The mechanical properties of the tissue medium generally deflect the needle, complicating what is already an inaccurate and imprecise needle guiding approach. Further, any changes or anisotropy in tissue mechanical properties may deflect the needle in a manner that is unpredictable to the surgeon, exacerbating the problem of inaccurate and imprecise needle targeting.

Accordingly, there is a need for a steerable needle that may be used for diagnostic and treatment purposes, wherein the needle may be steered through tissues of varying mechanical properties substantially without distorting the tissue medium. In the exemplary case of prostate cancer treatment, there is a need for a needle that may be steered to an optimal prostate capsule penetration angle. In the exemplary case of liver cancer treatment, there is a need for a needle that can apply multiple overlapping thermal ablations to a tumor without having to remove and reinsert the needle. In the exemplary case of ICH treatment, there is a need for a needle that may be steered through brain tissue medium to accurately and precisely target a clot while compensating for inaccurate burr hole placement.

SUMMARY OF THE INVENTION

The present invention provides a distal bevel-tip needle control device and algorithm that obviates one or more of the aforementioned problems due to the limitations of the related art. The present invention provides this by using a combination of software-based control models and image-based position feedback to steer the needle to a target position and orientation within a tissue medium.

Accordingly, one advantage of the present invention is that it improves the accuracy and precision of needle placement in medical diagnoses and treatments.

Another advantage of the present invention is that it reduces complications associated with needle insertion, tissue deflection, and tissue dislocation.

Still another advantage of the present invention is that it enables novel treatment methods.

Still another advantage of the present invention is that increases the accessibility of anatomical features to needles for the purposes of therapy and diagnostics.

Additional advantages of the invention will be set forth in the description that follows, and in part will be apparent from the description, or may be learned by practice of the invention. The advantages of the invention will be realized and attained by the structure pointed out in the written description and claims hereof as well as the appended drawings To achieve these and other advantages, the present invention involves a device for controlling a needle having a bevel. The device comprises a translation actuator; a rotation actuator; and a processor connected to the translation actuator and the rotation actuator, wherein the processor includes a memory encoded with a program for computing a needle path based on an orientation of the bevel and a mechanical property of a tissue medium.

In another aspect of the present invention, the aforementioned and other advantages are achieved by device for controlling a needle having a bevel, which comprises a translation actuator; a translation encoder; a rotation actuator; a rotation encoder; and a processor connected to the translation actuator, the translation encoder, the rotation actuator, and the rotation encoder, wherein the processor includes a memory encoded with a program for computing a needle path based on a first signal from the translation encoder and a second signal from the rotation encoder.

In another aspect of the present invention, the aforementioned and other advantages are achieved by a method for steering a needle having a bevel. The method comprises determining a desired position and orientation of the bevel; and computing a bevel translation speed and rotation angle based on the desired position and orientation of the bevel and a mechanical property of a tissue medium.

In another aspect of the present invention, the aforementioned and other advantages are achieved by a system for steering a needle having a bevel. The system comprises a medical imaging device; a needle control device; and a processor connected to the medical imaging device and the needle control device, the processor having a memory encoded with a program for acquiring an image, planning a needle path, and steering the needle along the needle path, wherein the program for steering the needle includes a program for controlling a needle translation speed and a bevel rotation angle.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 6A illustrates an image space and respective coordinate frames for the image space and bevel tip;

FIG. 6B illustrates an exemplary coordinate frame for the bevel tip; and

DETAILED DESCRIPTION OF THE ILLUSTRATED EMBODIMENTS

The present invention steers a needle with a bevel tip through a tissue medium by exploiting the pressure exerted by the tissue medium against the bevel as the needle is driven through the tissue. The pressure exerted on the bevel deflects the needle along a vector having a component perpendicular to the direction of motion of the needle. The extent of needle deflection is a function of the geometry and material properties of the needle, the mechanical properties of the tissue medium in which the needle is moving, and the linear velocity and angular orientation of the needle. By controlling the angular orientation of the bevel and the linear velocity of the needle, the needle may be steered or guided into a desired position and orientation. In doing so, the needle may be accurately and precisely steered toward an intended anatomical feature, such as a liver tumor, a brain clot, or a target area within a prostate. Further, the needle may be steered to locations previously inaccessible to needles, substantially enabling novel therapies and diagnostics.

By employing a software-based non-holonomic model, the known mechanical properties of the tissue medium may be used to derive linear velocity and angular orientation actuator commands. By using image-based feedback, the actual position and orientation of the tip of the needle may be compared with that predicted by the model. In doing so, the parameters pertaining to the mechanical properties of the tissue medium may be refined.

Figure 1:
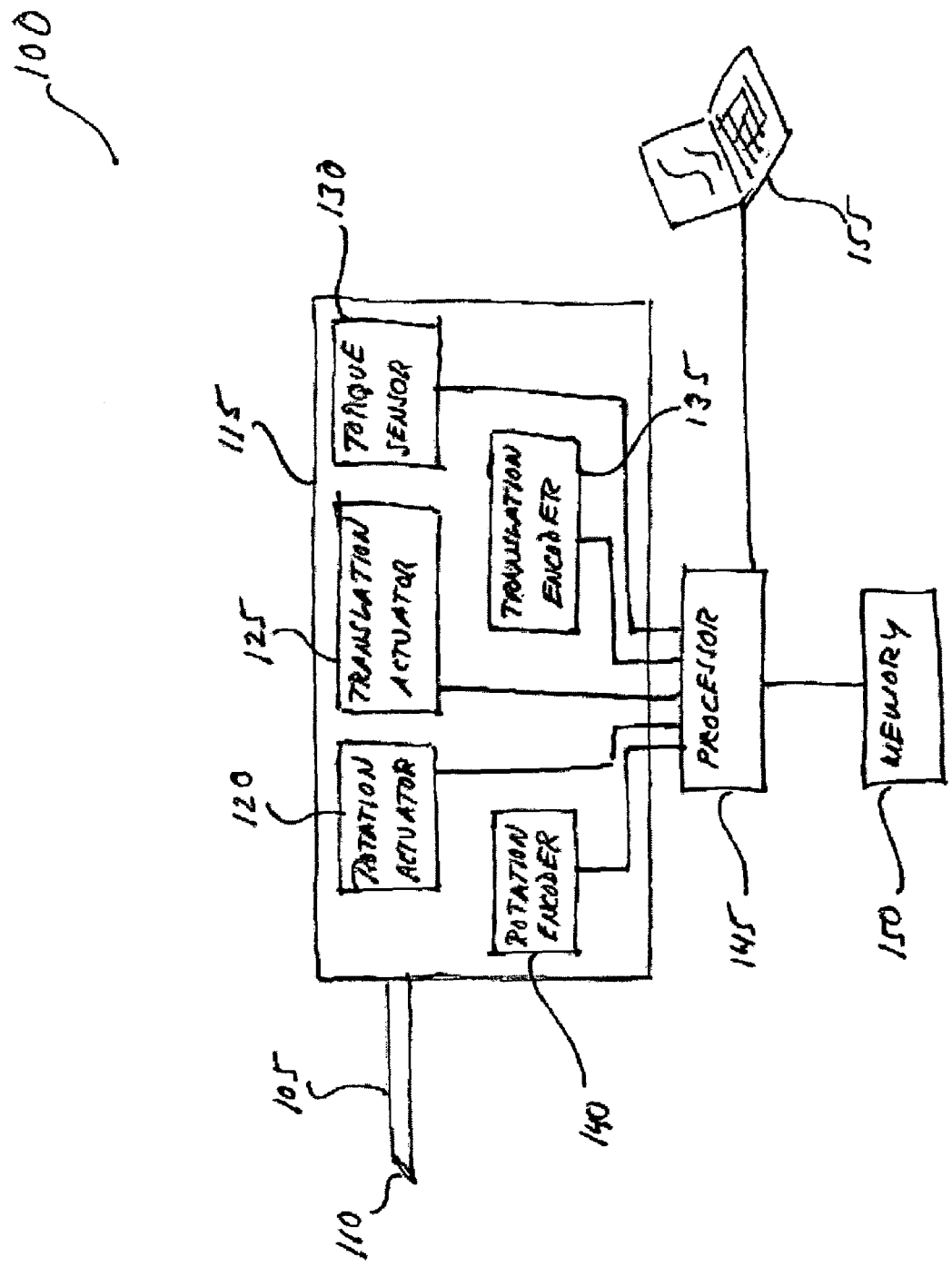
FIG. 1 illustrates an exemplary system for steering a bevel tipped needle according to the present invention.

FIG. 1 illustrates an exemplary system 100 for steering a needle through distal bevel-tip needle control according to the present invention. System 100 includes a needle 105 having a bevel tip 110, and a needle control device 115. Needle control device 115 includes a rotation actuator 120, a translation actuator 125, a rotation encoder 140, a translation encoder 135, and a torque/force sensor 130.

Needle control device 115 is connected to a processor 145, which is connected to a memory 150 and a user interface 155.

The mechanical properties of needle 105 may be such that it is less stiff than the expected stiffness of the tissue medium. By making needle 105 very flexible relative to the tissue medium, the needle does not displace a large amount of tissue in the process of being steered. Further, a sufficiently flexible needle will more precisely follow the path of bevel tip 110 as it is steered through the tissue medium. Needle 105 may be made of Nitinol, although other materials may be used, such as plastic. Needle 105 may be of 21, 22, or other desired gauge, depending on the intended use of the needle, the expected stiffness of the tissue medium, as well as other possible factors. In general, if needle 105 is to be guided though a stiffer tissue medium, the diameter of needle 105 may be increased (or a stiffer material may be used), as long as needle 105 does not become stiff so that does not follow the path of bevel tip 110 as it is steered, and it displaces tissue. The flexibility of needle 105 depends on the expected stiffness of the tissue to be penetrated. For example, for penetrating a stiffer tissue medium, needle 105 may be made of a stiffer material, or it may have a larger diameter, than would be required for a more flexible tissue medium. Needle 105 may have the configuration of a flexible drive shaft, or any configuration which is bendable but resists compression and torsion.

Another consideration in selecting material for needle 105 is that it be visible under to an imaging modality that may be used for image-based feedback.

Bevel tip 110 may be formed at the end of needle 105 at an angle relative to an axis defined by the axis of needle 105. Generally, a shallow bevel angle, e.g., about 5°, provides fo+r more steering control of needle 105 than a steep angle, such as about 80°, although both angles, and any angle between, provide for steering control. It will be readily apparent that other angles and bevel shapes are possible and within the scope of the invention.

Translation actuator 125 linearly translates needle 105. Translation actuator 125 may include an electric motor, such as a stepper motor, and may include a controller (not shown) connected between the stepper motor and processor 145. Exemplary motors include a VEXTA PK266-03A stepper motor, although other motors may be used, provided that the motor can provide sufficient force to make needle 105 penetrate the tissue medium. Exemplary controllers include a Velmex VXM-1 controller, although other controllers can be used, depending on the motor. One skilled in the art will readily appreciate that many variations of translation actuator 125 are possible and within the scope of the invention.

Rotation actuator 120 rotates needle 105. Rotation actuator 120 may include a similar motor and controller as translation actuator 125. However, differences in requirements may lead to different types of motors. For example, rotation actuator 120 may not need to provide the force that translation actuator 125 must provide. However, rotation actuator 120 may need to be able to provide for substantially precise angular orientation of bevel tip 110. As such, a different motor and controller may be used for rotation actuator 120 vs. translation actuator 125. It will be readily apparent to one skilled in the art than many different motors and controllers are possible for rotation actuator 120 and within the scope of the invention.

Rotation encoder 140 and translation encoder 135 respectively measure the degree of rotation and length of translation of needle 105 in response to forces imparted by rotation actuator 120 and translation actuator 125. Rotation encoder 140 and translation encoder 135 may include optical, mechanical, or magnetic encoders. Rotation encoder 140 and translation encoder 135 may be connected directly to processor 145, or may have separate signal conditioning components, which convert the encoders' signals into digital signals. It will be apparent to one skilled in the art that many implementations of rotation actuator 120 and translation encoder 135 are possible and within the scope of the invention.

Torque/force sensor 130 may include one or more sensors for measuring the force exerted by translation actuator 125 and the torque imparted on needle 105 by rotation actuator 120. Exemplary torque sensors include a Nano-17 torque sensor, although other sensors may be used. Torque/force sensor 130 may include one or more signal conditioning circuits, controllers, and/or interface circuits for communicating with processor 145.

Processor 145 provides control signals to, and receives data from, needle control device 115. Processor 145 also receives input from, and provides imagery and data to, user interface 155. Processor 145 is connected to memory 150, which is encoded with software (hereinafter "the software") for implementing processes associated with the present invention. Processor 145 may include multiple computers, including one or more embedded processors. If multiple computers are used, the software may run on multiple computers in a distributed manner. It will be readily apparent to one of ordinary skill that many architectures for processor 145 are possible and within the scope of the invention.

Figure 2:
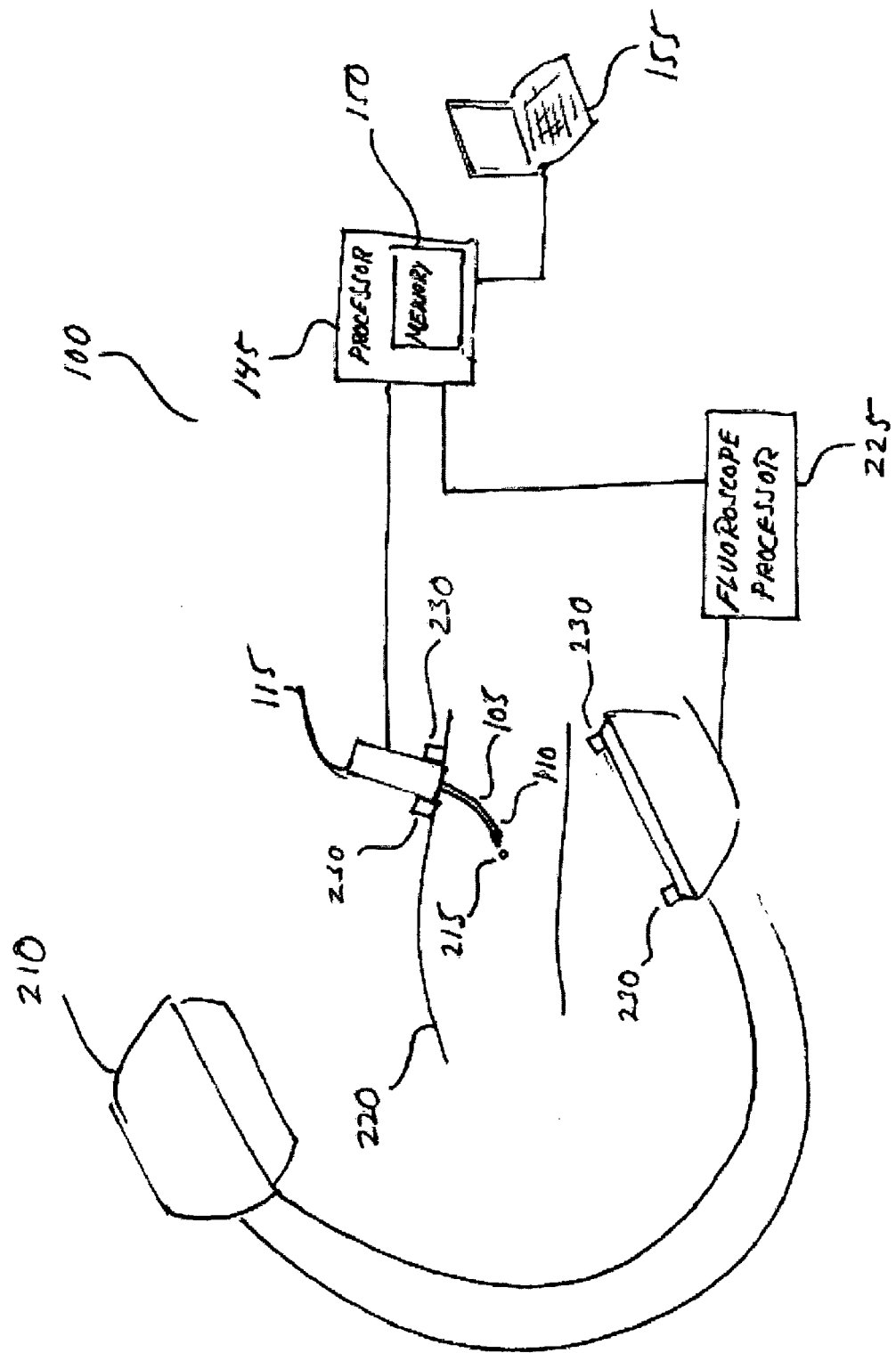
FIG. 2 illustrates the exemplary system of FIG. 1 being used in conjunction with a fluoroscope.

FIG. 2 illustrates system 100 being employed to steer needle 105 under image-based guidance using a fluoroscope 210. As illustrated in FIG. 2, a user, such as a surgeon, provides input via user interface 155 to processor 145, which issues steering commands to rotation actuator 120 and translation actuator 125 in needle control device 115. Rotation actuator 120 and translation actuator 125 drive needle 105, according to the steering commands, toward an intended target anatomical feature 215 within patient 220. Target anatomical feature of interest 215 may be a tumor, the target point within a prostate, a brain clot, etc. Fluoroscope 210 acquires imagery of needle 105 within patient 220. The fluoroscope processor 225 may provide imagery of needle 105 to processor 145. The process by which fluoroscope 210 provides image-based feedback to system 100 is described further below. Further illustrated in FIG. 2 are registration devices 230, which enable optical or magnetic registration of needle control device 115 and fluoroscope 210 to a common coordinate frame. Registration devices 230 may be optical or magnetic devices that are used in registration techniques that are known to the art. Registration devices 230 are optional.

Although FIG. 2 illustrates the use of fluoroscopy for providing image-based feedback, it will be apparent that other imaging modalities are possible and within the scope of the invention, provided that needle 105 is visible in the acquired images, such as ultrasound, Computed Tomography (CT), Magnetic Resonance Imaging (MRI).

Figure 3:
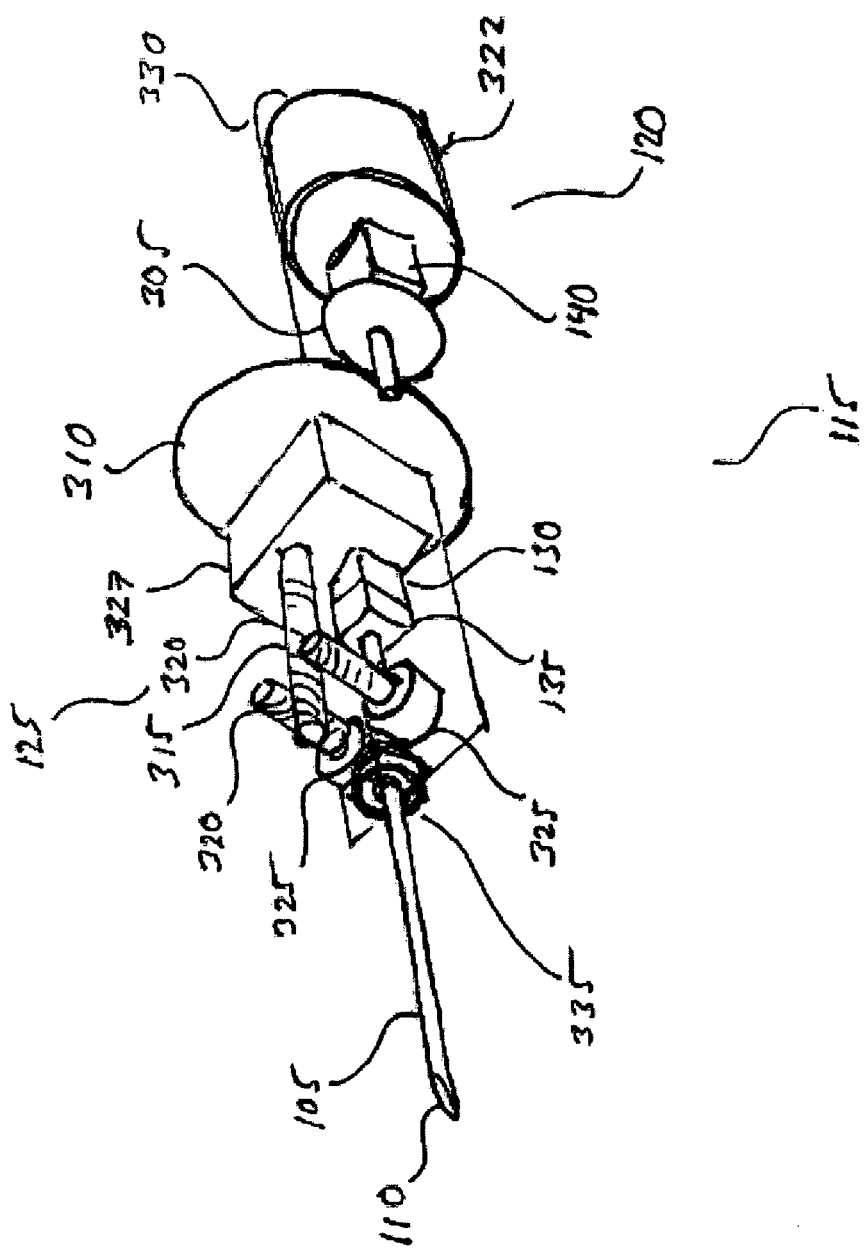
FIG. 3 illustrates an exemplary needle control device according to the present invention.

FIG. 3 illustrates a first exemplary needle control device 115 according to the present invention. FIG. 3 illustrates rotation actuator 120, translation actuator 125, rotation encoder 140, and translation encoder 135.

Referring to FIG. 3, translation actuator 125 includes a translation motor 327, which is connected to a worm drive 315. Worm drive 315 engages worm gears 320. Worm gears 320 are respectively connected to drive wheels 325. Drive wheels 325 are in direct and firm contact with needle 105. Slotted needle guide 330 substantially restricts motion of needle 105 to translation between, and in reaction to, drive wheels 325. Slotted needle guide 330 also substantially prevents needle 105 from rotating between drive wheels 325.

Needle control device 115 may also include a guide sheath 335 for preventing needle 105 from buckling as drive wheels 325 translate needle 105 into a tissue medium.

Rotation actuator 120 includes a rotation motor 322, and gears 305 and 310. As illustrated in FIG. 3, rotation actuator 120 may rotate the entire assembly that includes translation actuator 125.

Figure 4:
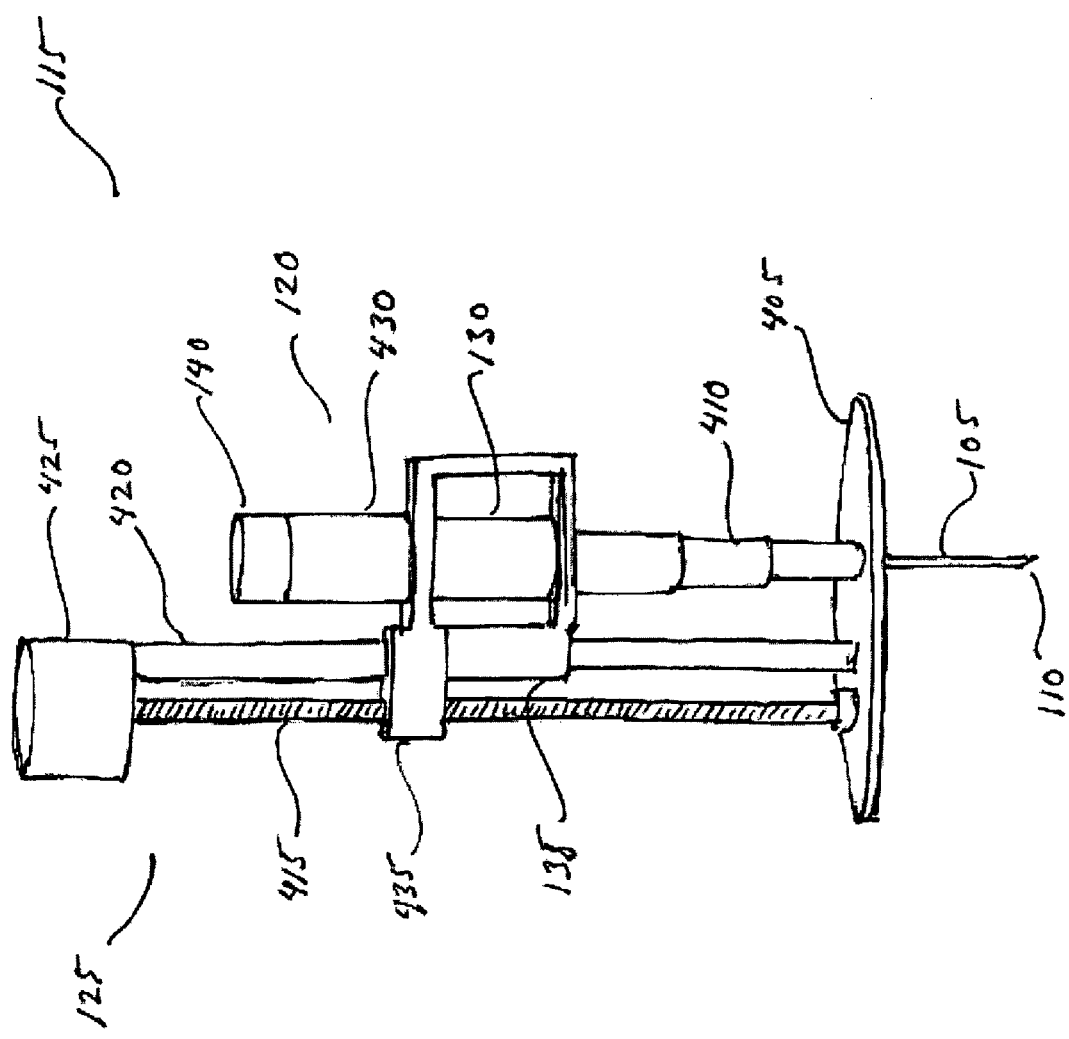
FIG. 4 illustrates another exemplary needle control device according to the present invention.

FIG. 4 illustrates a second exemplary embodiment of needle control device 115 according to the present invention. In this embodiment, needle control device 115 includes rotation actuator 120, translation actuator 125, rotation encoder 140, translation encoder 135, and torque/force sensor 130. This embodiment further includes a base 405, through which needle 105 is pushed by translation actuator 125. Translation actuator 125 includes a linear guide rail 420, a lead screw 415, and a motor 425 that drives lead screw 415. Threaded nut 435 engages lead screw 415, causing needle 105 and rotation actuator 120 to translate. As needle 105 translates, a telescoping guide 410 substantially prevents needle 105 from buckling.

Rotation actuator includes a motor 430, which is connected to rotational encoder 140. Rotation actuator 120 rotates needle 105 within telescoping guide 410. Torque/force sensor 130 may be a six-axis sensor. The length of linear guide rail 420 and lead screw 415 is a function of the anticipated length to which needle 105 is to be inserted into patient 220.

These embodiments of needle control device 115 are exemplary. Other configurations for needle control device 115 are possible and within the scope of the invention, provided that they provide two axes of control of needle 105: translational (along the axis of needle 105), and rotational (around the axis of needle 105).

FIG. 6A illustrates an image space 600, which is defined by coordinate basis vectors (x y z). Image space 600 may be a volume of interest within patient 220. Needle control device 115 is located toward an edge of image space 600. Target anatomical feature 215 is illustrated within image space 600. For the purposes of illustration, needle 105 is shown as having penetrated patient 220. Bevel tip 110, illustrated within image space 600, has a coordinate frame ($e_1$ $e_2$ $e_3$), which has a unique position and orientation within the (x y z) coordinate frame of image space 600. FIG. 6B illustrates the coordinate frame ($e_1$ $e_2$ $e_3$) of bevel tip 110.

Figure 5:
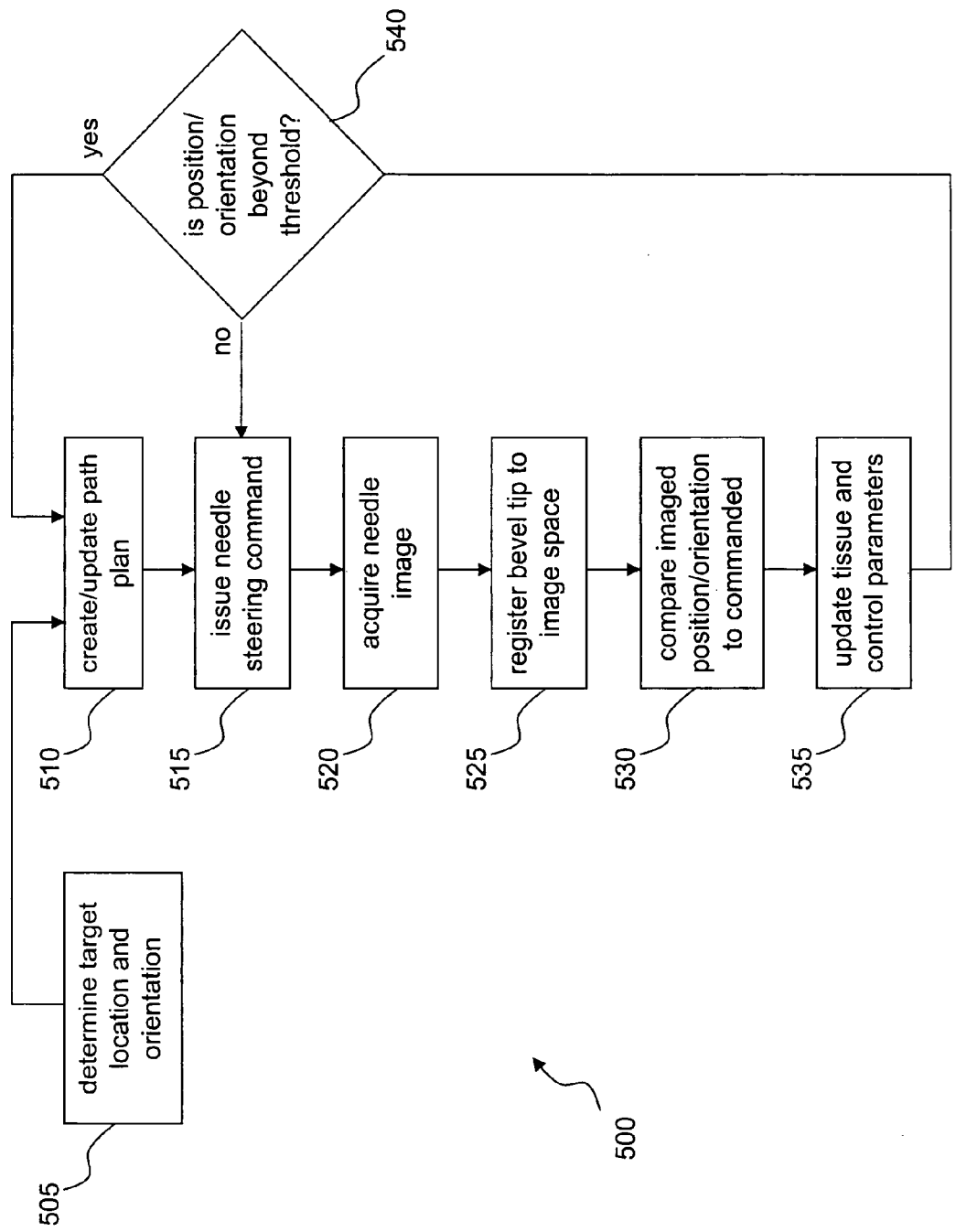
FIG. 5 illustrates an exemplary process for performing needle control according to the present invention.

FIG. 5 illustrates an exemplary process 500 for controlling the steering of needle 105 via distal bevel-tip needle control according to the present invention. All or part of process 500 may be performed by the software running on processor 145. Process 500 may be performed with system 100 operating in conjunction with fluoroscope 210, as illustrated in FIGS. 2 and 6A.

Referring to FIGS. 2 and 6A, at the initiation of process 500, needle control device 115 is placed against patient 220. Fluoroscope 210 acquires at least one image that encompasses intended target anatomical feature 215 within patient 220 and the point within patient 220 at which needle 105 will enter. Fluoroscope processor 225 may provide the software with the acquired imagery. The software then determines the position of needle control device 115 in the (x y z) coordinate frame of image space 600 by using registration devices 230 according to optical or magnetic registration techniques that are known to the art. Alternatively, if needle 105 has already been inserted, the software may determine the position and orientation of the coordinate frame ($e_1$ $e_2$ $e_3$) of bevel tip 110 in the (x y z) coordinate frame of image space 600.

Referring to FIG. 5, in step 505, the target location and orientation is determined. The target location and orientation refers to the desired final position and orientation of bevel tip 110, which may correspond to target anatomical feature of interest 215. In step 505, the software accepts commands from an surgeon via user interface, which indicate a desired position and orientation of bevel tip 110 of needle 105. The surgeon may determine the desired position and orientation of bevel tip 110 by acquiring an image via fluoroscope 210 and selecting a target point within image space 600 using user interface 155. To perform this, the surgeon may input a command into user interface 155, which is received by the software. Input may be done via a joystick or similar device by controlling a cursor in an image. The surgeon may then select the desired point to select the target location and orientation. In addition, if desired, the surgeon may select an initial entry position and orientation, or otherwise specify an initial entry area for the needle.

In step 510 the software plans the path of needle 105. In doing so, the software determines a sequence of commands using any of a variety of standard path planning (hereinafter "planning") techniques for kinematic systems of the form described below. If no specific entry point has been selected, planning may also include determining one or more suggested entry points for the needle within the initial entry area specified by the surgeon. To accomplish planning, the software computes the initial position and orientation of bevel tip 110, determines a desired path to the target location and orientation, and determines a sequence of commands to have bevel tip 110 follow the desired path. These commands are issued to translation actuator 125 and rotation actuator 120 that will result in bevel tip 110 having a final position and orientation corresponding to that input by the surgeon. The software computes the position and orientation of bevel tip 110 for a series of steps by implementing a non-holonomic kinematic model. An example of such a model is the "bicycle" model described below. It will be apparent to one skilled in the art that changes to needle tip geometry, material properties, and types and number of actuators may change the details of the model implemented, and that such changes are within the scope of the invention.

Figure 7:
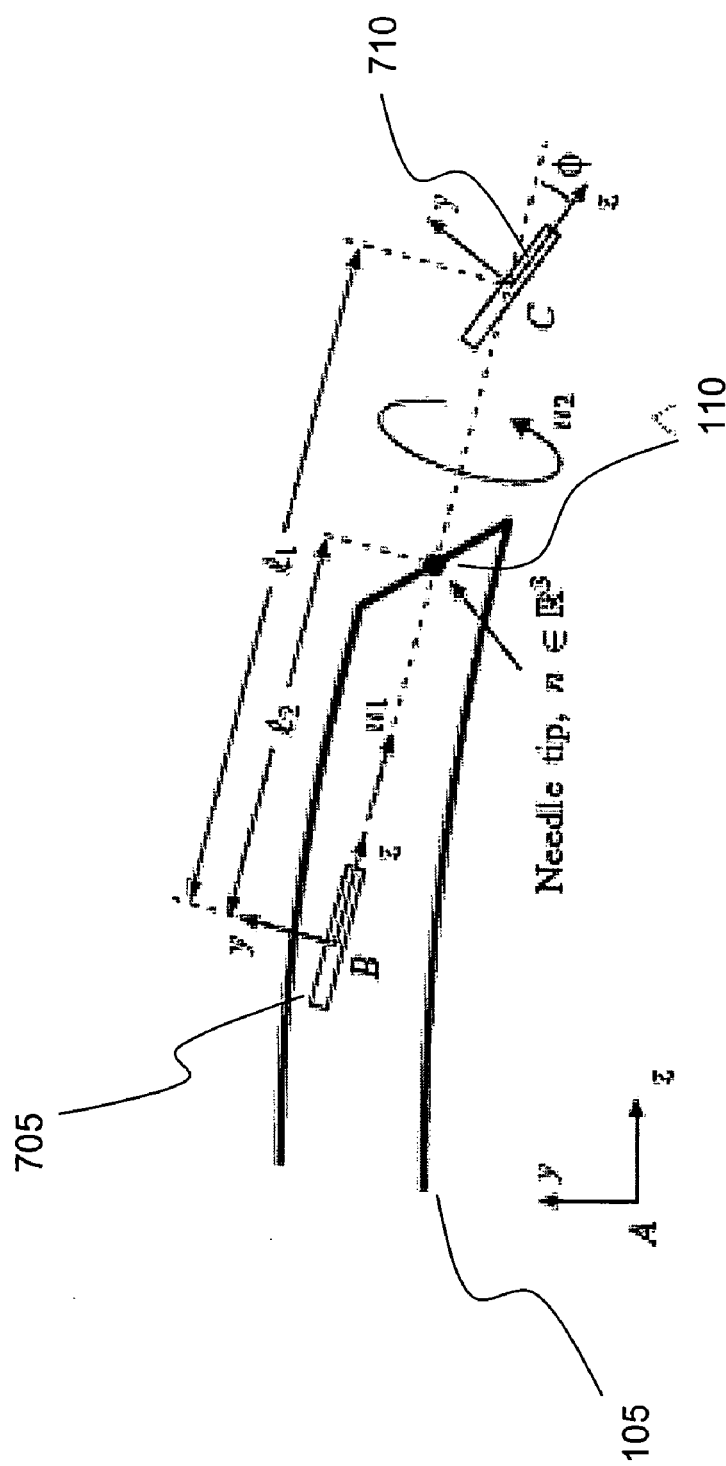
FIG. 7 illustrates the coordinate frames and hypothetical points of a control model according to the present invention.

FIG. 7 illustrates needle 105 and bevel tip 110 along with reference points corresponding to the bicycle model. According to the model, as the needle is inserted into patient 220, the tissue medium imposes a reaction force on bevel tip 110, deflecting it so that it follows an arc. The software may exploit this deflection, which is a function of the mechanical properties of the tissue medium, to steer needle 105 using needle translation and rotation as the control inputs.

Referring to FIG. 7, according to the bicycle model, two parameters correspond to the mechanical properties of the tissue medium: $l_2$, which is the distance from the "rear wheel" point 705 of the bicycle to bevel tip 110; and curvature κ. Parameters $l_2$ and κ may be visualized as follows. Consider rear wheel point 705 to be the rear wheel of a bicycle, and consider point 710 to be the front wheel. If front wheel point 710 is set at a fixed angle φ, then, depending on wheelbase $l_1$, the bicycle would follow a path having curvature κ, which is the inverse of the radius of the turn made by the bicycle. Parameter $l_2$ is one half of wheelbase $l_1$ and refers to the length from rear wheel point 705 along needle 105 to bevel tip 110. Parameters $l_2$ and κ are a function of the mechanical stiffness of the tissue medium, the mechanical properties of needle 105, and the angle of bevel tip 110. Curvature κ is the inverse of radius of curvature of deflection imparted on needle 105 due to the deflection force of the tissue medium on bevel tip 110. A given combination of tissue material and needle 105 will have a particular set of $l_2$ and κ parameter values. These values may be stored in memory 150 in the form of a database table. At initiation of process 500, the surgeon may select the tissue material through which needle 105 will be guided. The software may, in response, retrieve the appropriate $l_2$ and κ parameter values from memory 150.

Further to step 510, the software computes a 4×4 matrix corresponding to the translation and rotation of the center of bevel tip 110 for a sequence of steps. It does so according to the following relations.

$$g(k+1) = g(k) e^{(u_1(k)\hat{V}_1 + u_2(k)\hat{V}_2)T} \text{ and}$$

$$n(k) = R(k) l_2 e_3 + p(k)$$

where g(k+1) refers to the position and orientation of rear wheel point 705 with respect to the (x y z) coordinate frame for time sample k+1. Term g(k) is in a 4×4 special Euclidean group (SE(3)) expression of $$g(k+1) = \begin{bmatrix} R(k+1) & p(k+1) \\ 0^T & 1 \end{bmatrix},$$

where R(k+1) is the rigid rotation (a 3×3 rotation matrix) from the (x y z) coordinate frame of image space 600 to the new orientation of rear wheel point 705 given control inputs $u_1$ and $u_2$, and p(k+1) is the new position of rear wheel point 705 in the (x y z) coordinate frame of image space 600 given control inputs $u_1$ and $u_2$. The term n(k) refers to the position of needle bevel tip 110 in the (x y z) coordinate frame of image space 600 at time sample k. First control input $u_1$ is the translational speed of bevel tip 110, as imparted by translation actuator 125 and measured by translation encoder 135. Second control input $u_2$ is the rotation speed of bevel tip 110, as imparted by rotation actuator 120 and measured by rotation encoder 140; and T is the time period between sample k and k+1. $\hat{V}_1$ and $\hat{V}_2$ are differential elements of the Euclidean Group, the Matrix Exponential of which is a member of the Special Euclidean Group SE(3) described below. Accordingly, the update matrix $e^{(u_1(k)\hat{V}_1 + u_2(k)\hat{V}_2)T}$ represents the change in position and orientation of needle 105 during time step k. $\hat{V}_1$ corresponds to translation of needle 105, wherein the linear velocity v of bevel tip 110 is along $e_3$, and angular velocity ω is around $e_1$ in the form of matrix $$V_1 = \begin{bmatrix} v \\ \omega \end{bmatrix} = \begin{bmatrix} e_3 \\ \kappa e_1 \end{bmatrix}.$$

$\hat{V}_2$ corresponds to the rotation of bevel tip 110 around $e_3$ such that $$V_2 = \begin{bmatrix} 0 \\ e_3 \end{bmatrix}.$$

Term g(k) is the previous orientation and position of rear wheel point 705 at time sample k. Term g(k) refers to the position and orientation of rear wheel point 705 with respect to the (x y z) coordinate frame. Term g(k) is in a 4×4 special Euclidean group (SE(3)) expression of $$g(k) = \begin{bmatrix} R(k) & p(k) \\ 0^T & 1 \end{bmatrix},$$

where R(k) is the rigid rotation from the (x y z) coordinate frame of image space 600 to rear wheel point 705 at time sample k, and p(k) is the position of rear wheel point 705 in the (x y z) coordinate frame of image space 600 at time sample k. Such mathematical relations are further discussed in Murray, R. M., Li, Z., and Sastry, S. S. 1994. *A Mathematical Introduction to Robotic Manipulation*. CRC Press, Ann Arbor Mich., which is incorporated by reference as if fully disclosed herein. Needle path planning is discussed in *Steering Flexible Needles Under Markov Motion Uncertainty*, Ron Alterovitz and Andrew Lim and Ken Goldberg and Gregory S. Chirikjian and Allison M. Okamura, IEEE International Conference on Intelligent Robotics and Systems (IROS), August 2005, which is incorporated by reference as if fully disclosed herein.

Using relations for g(k+1) and n(k), the software computes a path of bevel tip 110 and selects a series of control inputs $u_1$ (translation) and $u_2$ (rotation) that results in a path that may achieve the target location and orientation of bevel tip 110. The software may do this by iteratively computing the above relations and converging on a set of $u_1$ and $u_2$ that provides the closest path to that desired. Alternatively, the software may execute algebraically inverted versions of the above relations such that the desired $u_1$ and $u_2$ are results. It will be readily apparent to one of ordinary skill that multiple algorithmic approaches to computing $u_1$ and $u_2$ are possible and within the scope of the invention.

In step 515, the software issues the commands to provide translation actuator 125 with control input $u_1$ and rotation actuator 120 with control input $u_2$ according to the series of control inputs.

In step 520, fluoroscope 210 acquires one or more images of image space 600, including needle 105. Fluoroscope processor 225 provides the software with the images, which are subsequently displayed by user interface 155.

Step 520 may run continuously throughout process 500. Alternatively, step 520 may be executed periodically, such as at the beginning and end of each control input generated in step 510. It will be readily apparent to one of ordinary skill that variations to the timing of fluoroscope images are possible and within the scope of the invention.

In step 525, the software registers the location of bevel tip 110 in the image acquired by fluoroscope 210. In doing so, the software identifies the needle 105 and bevel tip 110 in the image, determines which voxel or voxels correspond to the bevel tip, and then determines the location of the corresponding voxels. The result of step 525 is a position and orientation of bevel tip 110 in the (x y z) coordinate frame of image space 600. Step 525 may be performed for every image acquired by fluoroscope 210, or for intermittently acquired images.

In step 530, the software compares the registered position and orientation of bevel tip 110 (from the fluoroscope image) with the expected position and orientation along the path planned in step 510 according to the bicycle model. The result is the deviation between the actual and expected position and orientation of the coordinate frame ($e_1$ $e_2$ $e_3$) of bevel tip 110.

In step 535, the software updates tissue medium parameters $l_2$ and $\kappa$ and may update control inputs $u_1$ and $u_2$. If there is any deviation between the actual and expected position and orientation, it may be due to an inaccuracy in tissue medium mechanical parameters $l_2$ and $\kappa$. This may occur due to uncertainties in parameter values corresponding to a tissue type, or it may be due to bevel tip 110 passing through a tissue interface and entering a tissue having different mechanical properties. In either case, the software may estimate a new set of values for $l_2$ and $\kappa$ that will resolve the discrepancy between the actual and the expected position and orientation of bevel tip 110. The software may store the new $l_2$ and $\kappa$ values. Further, the software may determine a new set of control inputs $u_1$ and $u_2$, which may more effectively guide bevel tip 110 along the path planned in step 510.

In step 540, the software determines if it is necessary to plan a new path. If the deviation computed in step 530 is above a certain threshold, feedback-based adjustments of model parameters $l_2$ and $\kappa$ and control inputs $u_1$ (translation) and $u_2$ rotation may not be enough to have needle 105 follow the planned path. In this case, the software may return to step 510 to plan a new path, given the current orientation and position of bevel tip 110. Otherwise, the software may return to step 515 to issue new actuator commands that reflect the newly computed control inputs $u_1$ (translational) and $u_2$ (rotational).

The software may iterate process 500. In doing so, the software may return to step 510 to update the path plan, if the deviation computed in step 530 is greater than a certain threshold. If the deviation is below this threshold, the new control inputs $u_1$ and $u_2$ may be sufficient to minimize the deviation in the subsequent iteration of process 500.

Variations to system 100 and process 500 are possible and within the scope of the invention. For example, either embodiment of needle control device 115 may include one or more manual overrides (not shown) that may enable a surgeon to manually control one or both of translation actuator 125 and rotation actuator 120.

Further, process 500 may enable a surgeon to provide direct control of either control inputs $u_1$ and $u_2$. For example, as the surgeon directly controls $u_1$ (translational), either manually or through keyboard or joystick control, the software may compute the corresponding control input $u_2$ (rotational). Alternatively, the surgeon may directly control $u_2$ while the software controls $u_1$. Further, the software may enable the surgeon to control both $u_1$ and $u_2$ via manual, keyboard, or joystick control. In this case, the software may enable the surgeon to switch control between direct control and software control according to process 500. One skilled in the art will readily recognize that many such variations are possible and within the scope of the invention.

In another variation, either or both of the translation actuator 125 and rotation actuator 120 may have no motor. In this case, the actuator or actuators may have knobs or dials that provide direct manual control only. The knobs may respectively be connected to translation encoder 135 and the rotation encoder 140, which are in turn connected to processor 145. In this case, the software may "steer" the needle by providing information to the surgeon via user interface 155 indicating the estimated path of bevel tip 110 corresponding to the surgeon's manual control.

In another variation, step 525 may only register the position of bevel tip 110 (as opposed to position and orientation) and step 530 may only compare the actual position of bevel tip 110 to the expected position of bevel tip 110.

In another variation, the angle of bevel tip 110 is variable and may be changed by a third actuator (not shown).

Although step 510 describes the use of a bicycle kinematic model, other non-holonomic kinematic models may be used. For example, the software may use a "unicycle" model in place of the bicycle model. In this case, the parameter $l_2$ is set to zero and the "front wheel" is disregarded. The unicycle may have the benefit of being less computationally intensive, which may enable it to be executed on a smaller or slower processor, although it may not be as robust as the bicycle model. Further, other models, which correspond to a particular geometry of bevel tip 110, material properties, and actuator configurations used for needle steering may lead to different definitions for vectors $V_1$ and $V_2$, and may require additional vectors $V_3$, $V_4$, etc.

In another variation, registration devices 230 and step 535 of process 500 may be omitted. In this variation, registration is not used, and the deviation determined in step 530 is done visually by the surgeon via fluoroscope images displayed on user interface 155. In this case, the surgeon navigates bevel tip 110 using anatomical visual references within the images.

Although the above description may be applicable to treatment of prostate cancer, liver cancer, and ICH, it will be readily apparent the above-described system and process may be applied to any number of needle-based therapies and diagnostics.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A device for controlling a needle having a bevel, comprising:
    a translation actuator;
    a rotation actuator; and
    a processor connected to the translation actuator and the rotation actuator, wherein the processor includes a memory encoded with a program for computing a needle path based on a desired end position of the needle, estimated properties of the needle and a tissue, a rotation angle of the bevel, and a translation speed of the needle.

2. The device of claim 1, wherein the program for computing the needle path comprises instructions for computing the needle path based on a mechanical property of the tissue.

3. The device of claim 1, wherein the memory is further encoded with a program for computing a first control input and a second control input, wherein the first control input and the second control input correspond to the computed needle path.

4. The device of claim 1, further comprising a translation encoder connected to the processor.

5. The device of claim 1, further comprising a rotation encoder connected to the processor.

6. The device of claim 1, further comprising a needle having a bevel, wherein the bevel has an angle of about 5°.

7. The device of claim 1, further comprising a needle, wherein the needle is flexible.

8. A device for controlling a needle having a bevel, comprising:
    a translation actuator;
    a translation encoder;
    a rotation actuator;
    a rotation encoder; and
    a processor connected to the translation actuator, the translation encoder, the rotation actuator, and the rotation encoder, wherein the processor includes a memory encoded with a program for computing a needle path based on a first signal from the translation encoder that represents a translation speed of the needle, and a second signal from the rotation encoder that represents a rotation angle of the bevel.

9. The device of claim 8, wherein the translation actuator is manually controlled.

10. The device of claim 8, wherein the rotation actuator is manually controlled.

11. The device of claim 1, further comprising a needle, wherein the needle comprises Nitinol.

12. The device of claim 8, further comprising a needle, wherein the needle comprises Nitinol.

\* \* \* \* \*

UNITED STATES PATENT AND TRADEMARK OFFICE
CERTIFICATE OF CORRECTION

PATENT NO. : 7,822,458 B2
APPLICATION NO. : 11/436995
DATED : October 26, 2010
INVENTOR(S) : Webster, III et al.

Page 1 of 1

It is certified that error appears in the above-identified patent and that said Letters Patent is hereby corrected as shown below:

Title Page, Item "(73) Assignee:" the patent should be corrected to read as follows:

--The Johns Hopkins University, Baltimore, MD (US); and

The Regents of the University of California, Oakland (CA)--.

Signed and Sealed this
Twenty-sixth Day of April, 2011

David J. Kappos
*Director of the United States Patent and Trademark Office*